(12) United States Patent
Moertelmaier

(10) Patent No.: US 9,239,292 B2
(45) Date of Patent: Jan. 19, 2016

(54) METHOD AND APPARATUS FOR TRACKING THE MOTION OF MOLECULES IN A MICROSCOPE

(71) Applicant: Keysight Technologies, Inc., Minneapolis, MN (US)

(72) Inventor: Manuel Moertelmaier, Linz (AT)

(73) Assignee: Keysight Technologies, Inc., Santa Rosa, CA (US)

( * ) Notice: Subject to any disclaimer, the term of this patent is extended or adjusted under 35 U.S.C. 154(b) by 311 days.

(21) Appl. No.: 13/847,992

(22) Filed: Mar. 20, 2013

(65) Prior Publication Data

US 2013/0252272 A1    Sep. 26, 2013

Related U.S. Application Data

(60) Provisional application No. 61/614,419, filed on Mar. 22, 2012.

(51) Int. Cl.
*G01N 21/64*    (2006.01)
*G02B 21/16*    (2006.01)
*G02B 21/00*    (2006.01)

(52) U.S. Cl.
CPC ............ *G01N 21/64* (2013.01); *G01N 21/6428* (2013.01); *G01N 21/6458* (2013.01); *G02B 21/0076* (2013.01); *G02B 21/16* (2013.01)

(58) Field of Classification Search
CPC . G01N 21/64; G01N 21/6428; G02B 21/0076
USPC ........................................... 250/458.1–461.2
See application file for complete search history.

(56) References Cited

U.S. PATENT DOCUMENTS

| | | | |
|---|---|---|---|
| 2003/0092884 A1* | 5/2003 | Lukyanov et al. | 530/350 |
| 2008/0149867 A1* | 6/2008 | Konishi et al. | 250/582 |
| 2008/0217557 A1* | 9/2008 | Courtney et al. | 250/459.1 |
| 2010/0140506 A1* | 6/2010 | Eggeling et al. | 250/459.1 |

FOREIGN PATENT DOCUMENTS

WO     2011/029459 A1    3/2011

OTHER PUBLICATIONS

Eggeling, et al., Reversible Photoswitching Enables Single-Molecule Fluorescence Fluctuation Spectroscopy at High Molecular Concentration, Microscopy Research and Technique 7:1003-1009, Jul. 27, 2007, Wiley InterScience, www.interscience.wiley.com.
Bohme, et al., Illuminating the life of GPCRs, Cell Communication and Signaling 2009 7:16, Jul. 14, 2009, BioMed Central, http://www.biosignaling.com/content/7/1/16.

* cited by examiner

*Primary Examiner* — Casey Bryant
*Assistant Examiner* — Jeremy S Valentiner

(57) ABSTRACT

An apparatus and method for measuring the mobility of molecules in a sample are disclosed. Molecules in a sample are tagged with a dye having active and inactive states that are generated by exposing dye to light of an activation wavelength and an inactivation wavelength, respectively, the activation wavelength being different from the inactivation wavelength. The sample is illuminated in a microscope with a light pattern that includes a first region in which the dye is activated and a second adjacent region in which the first dye is inactivated. After the sample is so illuminated, an image of the activated first molecules is recorded when the first molecules are illuminated with light of an excitation wavelength. Molecules having the first dye in the inactive state are distinguishable from molecules having the first dye in the active state in the microscope when illuminated with light of the excitation wavelength.

18 Claims, 4 Drawing Sheets

METHOD AND APPARATUS FOR TRACKING THE MOTION OF MOLECULES IN A MICROSCOPE

CROSS-REFERENCE TO RELATED PATENT APPLICATIONS

This application is a conversion of, and claims priority therefrom, of U.S. Provisional Patent Application 61/614,419 filed on Mar. 22, 2012, said patent application being incorporated by reference herein.

BACKGROUND

The interaction of molecules on the surface of living cells is of great interest to biologists. In many cases, the interaction partners are mobile, so their common movement can be used as proxy information on their interaction. The size of intermolecular interaction regions is of the order of 10-100 nm. Hence, an analysis based on imaging the two molecules with a light microscope is of limited value, since the resolution limit of a light microscope is about 300 nm. Since the measurements are to be made on living cells, electron microscopes cannot be utilized. Optical super-resolution techniques can, in principle, provide the required resolution. However, the time required to form a high-resolution image with such techniques is too long to observe the co-localization or co-movement of typically mobile molecules. In particular, the molecules in question travel significant distances during the imaging process, and hence, the resolution is blurred by the molecular motion. It is inherently difficult to reduce this effect by lowering the imaging time, as the molecules show diffusion, where the expected displacement over time increases with the square root of the time. Hence, a four-fold reduction in imaging time will only result in a two-fold reduction of motion blur.

Foerster Resonant Energy Transfer (FRET) attempts to overcome these problems by labeling the molecules in question with two appropriately chosen different dyes. If the molecules in question approach one another within about 5 nm, a shift in the color of the florescence emission occurs. However, to detect the shift, there must be a significant relative number of molecules within 5 nm of each other. Since molecules do not usually approach one another within this distance for a prolonged time, the fraction of the molecules contributing to the shifted spectrum is often too small to be detected. In addition, molecules can still reliably interact, e.g. through a third intermediary partner, but mostly remain separated more than ~10 nm, preventing FRET. An example where such a situation is expected to occur is within hypothesized structures called lipid rafts. Here, lipids in the cell membrane form islets which are enriched in certain molecule species. However, the molecules within the rafts are thought to be mobile, and are not expected to be packed tightly enough to result in observable FRET.

Fluorescence Correlation Spectroscopy (FCS) attempts to overcome the resolution problems by inferring that the molecules move together. Consider the case in which one wishes to determine if a first molecule moves with a second molecule. In FCS, the first molecules are tagged with a first label, and the second molecules are tagged with a second label having a different color. Only a small region of the cell's membrane is illuminated (a spot about 300 nm in diameter). The optical emission from the region is recorded at very high speeds. Since the region is large enough to accommodate many molecules of both species at the same time, there will always be a signal with both colors. That signal will vary over time depending on the molecular movements. If the molecules are mobile and travel together, the changes in signals among the two color channels will be correlated. If the two molecules do not travel together, the channels will be uncorrelated. In practice, the signals are very noisy and require statistical post processing to detect any co-localization.

Another proposed solution is referred to as Thinning Out Clusters While Conserving the Stoichiometry of Labeling (TOCCSL). Here, the target molecules are also labeled with fluorescent dyes. A small region of the cell's membrane is photo-bleached exhaustively using a laser beam to eliminate fluorescence from the target molecules in that region. Subsequently, diffusion of the molecules leads to a gradual exchange of molecules between the bleached region and its surroundings. After a time of typically less than a second, an image of the bleached region is taken with a light microscope. At that time, only a small number of bleached (now invisible) molecules will have been replaced by non-bleached (visible) molecules. Hence, the visible molecules will be, on average, separated by a distance of about 1 micron in the formerly bleached region. At this separation, the unbleached molecules that have moved into the bleached region will appear as individual fluorescent spots. By measuring the brightness of a spot and the number of dye molecules in the spot, the number of molecules of interest in that spot can be determined. If the molecules do not move together, each spot would be expected to have a brightness consistent with that of a single dye molecule. If the molecules move in clusters of N molecules, then the brightness of the spot would be N times greater. If two-color labeling is used for two different species of molecules, the color ratio of the spots provides information on the relative composition of the molecule clusters. Finally, if the time between bleaching and imaging is varied, the temporal stability of the clusters on a time frame of the order of milliseconds to seconds can be determined.

This technique assumes that groups of molecules are either fully bleached or unbleached. The main problem with the TOCCSL technique is that the border of the bleached region is slightly blurred due to the optical resolution limit of the bleaching light beam. In addition, some molecules move back and forth between the bleached region and non-bleached region during the bleaching process. As a result, the groups in this region will not necessarily be completely bleached. These partially bleached groups complicate the interpretation of the data. Accordingly, a method that reduces the number of partially-bleached groups is needed.

SUMMARY

Embodiments of the present invention include an apparatus and method for measuring the mobility of molecules in a sample. The method includes tagging first molecules in a sample with a first dye, the first dye having an active state that is generated by exposing the first dye to light of an activation wavelength and an inactive state that is generated by exposing the first dye to light of an inactivation wavelength, the activation wavelength being different from the inactivation wavelength. The sample is illuminated in a microscope with a light pattern that includes a first region in which the first dye is activated and a second adjacent region in which the first dye is inactivated, to generate activated and inactivated first molecules. After the sample is so illuminated, an image of the activated first molecules is recorded when the first molecules are illuminated with light of an excitation wavelength. The region so illuminated may include a significant fraction of the second region, but can also encompass all of the second and first regions. Molecules having the first dye in the inactive state are distinguishable from molecules having the first dye in the active state in the microscope when illuminated with light of the excitation wavelength.

In an aspect of an embodiment of the invention, an image is recorded at a first time after illuminating the sample with the light pattern. The first time is chosen such that activated molecules have moved a sufficient distance to allow individual clusters of activated molecules to be viewed separately with the microscope.

In another aspect of an embodiment of the invention, a second image of the sample illuminated by the excitation wavelength is recorded at a second time, the first time differing from the second time by an amount sufficient to detect motion of the activated molecules in the sample.

In another aspect of an embodiment of the invention, the intensity of light emitted from a cluster of first molecules in the first image is recorded to determine the number of tagged molecules present in the cluster.

In a still further aspect of one of the embodiments of the invention, second molecules in the sample are tagged with a second dye, the second dye having an active state that is generated by exposing the second dye to light of an activation wavelength and an inactive state that is generated by exposing the second dye to light of an inactivation wavelength. The activation and inactivation wavelengths for the second dye can be identical to or different from the ones for the first dye. The second dye emits light of a wavelength different from the first dye when illuminated with its excitation wavelength, which can be the same as, or different from the first excitation wavelength. The ratio of intensities of light from the first and second dyes in the first image is measured.

DETAILED DESCRIPTION

The present invention is based on the observation that there are photo-convertible dyes that can be switched from a first state, referred to as the "active state", to a second state, the "inactive state", using two different wavelengths of light. The dyes in the inactive state can be differentiated from the dyes in the active state. For example, a dye in the inactive state can have an emission that is absent or only weakly present in a fluorescence micrograph. In another example, the dye in the inactive state emits light of a different color from light in the active state, and hence, the two states can be differentiated using an appropriate set of emission and/or dichroic filters that render the dye in the inactive state substantially invisible in that the intensity of light from that dye molecule is substantially different from the intensity of light from a dye molecule in the active state. The filters are chosen such that the dyes in the active state are detected in that micrograph. To simplify the following discussion, a molecule that is tagged with a dye in the active state will be referred to as an "active molecule", and a molecule that is tagged with a dye in the inactive state will be referred to as an "inactive molecule".

Refer now to FIGS. 1A-1D, which illustrate a population of molecules that are subjected to the method of the present invention at various stages in the method. Initially, the population includes a random mixture of molecules in the active and inactive states. The molecules in the active state are indicated by the filled circles, molecule 11 being exemplary of an active molecule. The molecules in the inactive state are indicated by open circles, molecule 12 being exemplary of an inactive molecule.

Figure 1C:
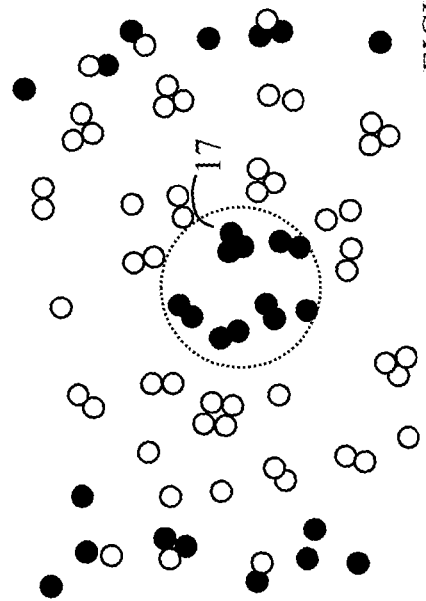
FIGS. 1A-1D illustrate a population of molecules that are subjected to the method of the present invention at various stages in the method.
Figure 1D:
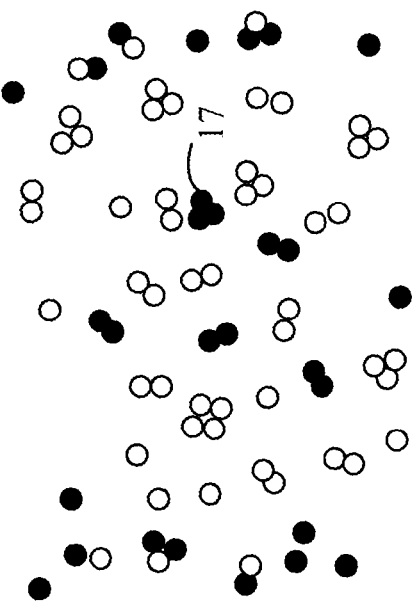
Figure 1A:
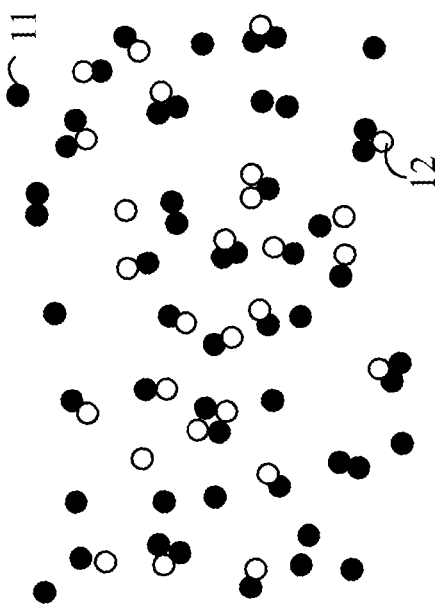
Figure 1B:
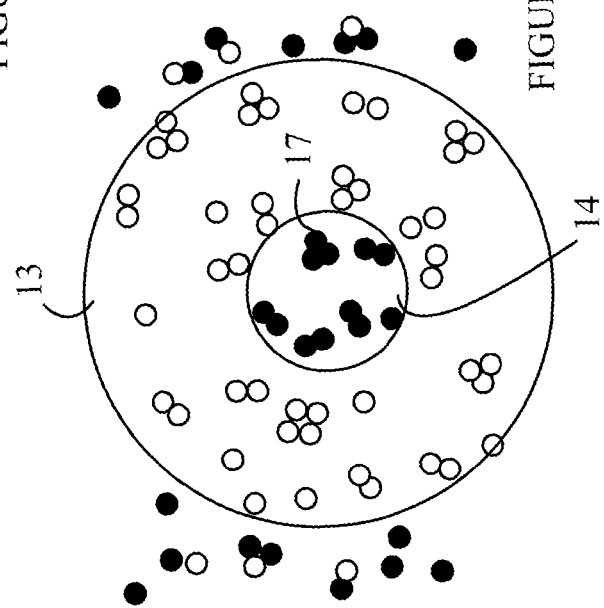

Refer now to FIG. 1B. The field of molecules shown in FIG. 1A is exposed to a two-color light pattern in which the light in region 13 is of the wavelength that inactivates the molecules, and the light in region 14 activates the molecules in that region.

This complementary illumination pattern sharpens the boundary between the active and inactive molecules. Consider a molecule that is initially in region 14 and that has been placed in the active state. If that molecule is near the boundary between regions 13 and 14 and wanders into region 13, it will be converted to the inactive state. Without the complementary illumination, that molecule would have remained in the active state, thus blurring the boundary between the two regions.

When the activation illumination is turned off, the molecules in the active state will be concentrated in region 14 as shown in FIG. 1C. The molecules in the field will continue to move randomly resulting in molecules from both regions mixing with one another as shown in FIG. 1D. Since the active molecules that were in region 14 will move into region 13 where all of the molecules were rendered inactive, i.e., invisible, the activated molecules can be followed under the microscope using an illumination wavelength that allows the active molecules to be distinguished from the inactive molecules as the active molecules are surrounded by inactive molecules. For example, molecular cluster 17 shown in FIG. 1B can be followed as an individual object as it wanders out into region 13, as it is now surrounded by molecules that are inactive as shown in FIG. 1D.

It should be noted that the density of active molecules in region 14 at the end of the activation illumination is too great to allow individual molecules or clusters of molecules to be seen as individual, separate objects, in light microcopy. It is only after these active molecules are diluted with the inactive molecules from region 13 that the active molecules or clusters of molecules can be individually distinguished from one another using light microscopy. Hence, by recording images of the activated molecules with light of the excitation wavelength as a function of time, the movement of the molecules in the active state can be followed.

Figure 2:
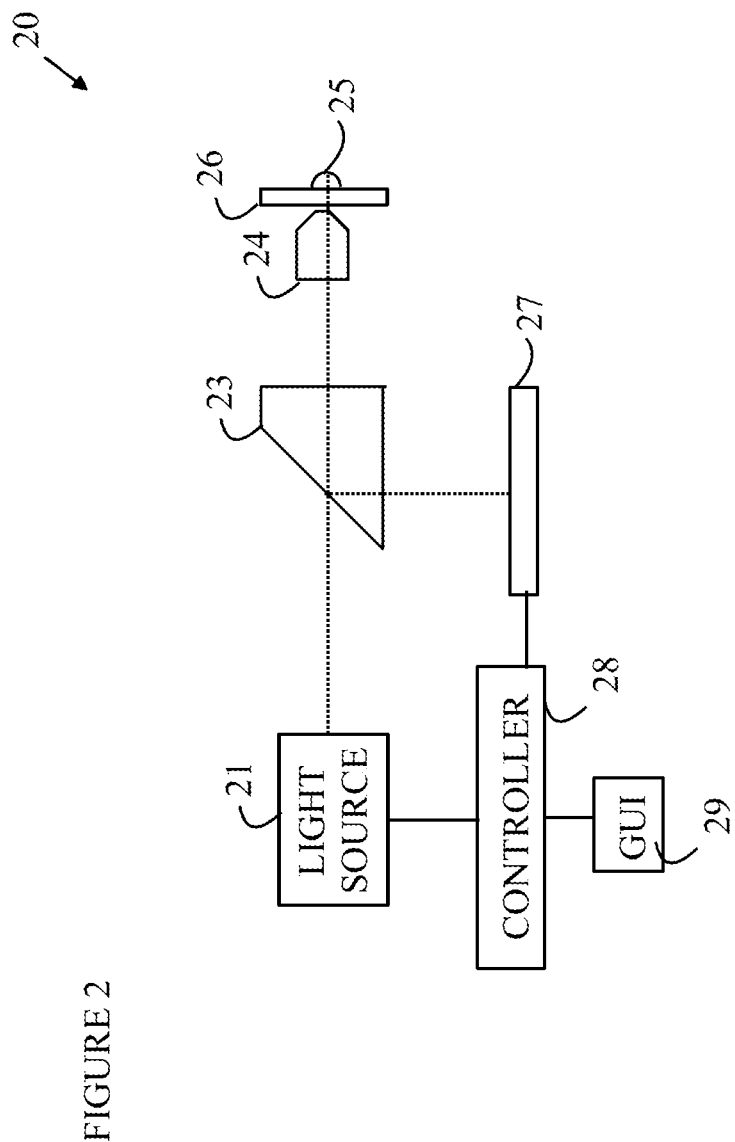
FIG. 2 illustrates a fluorescence microscope that can be utilized for practicing the method of the present invention.

The present invention can be practiced on a number of different light microscope platforms. In embodiments in which the active molecules are tracked using a fluorescent tag, a fluorescence microscope arrangement is preferred. Refer now to FIG. 2, which illustrates a fluorescence microscope that can be utilized for practicing the method of the present invention. Microscope 20 views a sample 25 that is located on a slide 26. Sample 25 has been stained with a fluorescent dye that is emits light in a first band of wavelengths when excited by light in a second band of wavelengths. A light source 21 illuminates sample 25 via objective lens 24 with light in the second band of wavelengths via a dichroic beam splitter 23 that lets light pass from light source 21, but reflects light in the first band of wavelengths. The light reflected by dichroic beam splitter 23 is imaged into a camera 27. Camera 27 is typically under the control of a controller 28 that includes a graphical user interface (GUI) 29 for interacting with the person performing the experiment. Camera 27 records images of the sample in response to signals entered through GUI 29.

To simplify the following discussion, the first band of wavelengths will be referred to as the "emission" band, and the second band of wavelengths will be referred to as the "excitation" band. The band of wavelengths that activates the dye will be referred to as the "activation" band, and the band of wavelengths that inactivates the dye will be referred to as the "deactivation" band.

Light source 21 needs to be able to generate light in the activation band, the deactivation band and the excitation band. For some fluorescent dyes, the excitation and deactivation bands will be identical, or overlap. Depending on this, the light source will have to be able to create two or three different wavelengths. In the case in which the excitation and deactivation bands are the same, fluorescence emission and deactivation are competing processes. That is, while the dye is being excited, it may also become inactivated. Until the dye is inactivated, it emits light at the detected wavelength in the fluorescence micrograph. The excitation intensity, and the exposure time for imaging, must be chosen according to the experimental needs of the methods described here. For example, if only a single image is to be taken of the active molecules after the initial activation and inactivation of different regions, then a high excitation intensity and long exposure time can be chosen to maximize the fluorescence signal. If, however, subsequent images are to be taken, a low excitation intensity and a shorter exposure time should be selected, as each exposure may partially inactivate clusters of active molecules.

The activation band wavelength and deactivation band wavelength are preferably generated simultaneously with different illumination patterns to provide the activated region and inactivated region in the field of view. However, embodiments in which the activation and inactivation patterns are provided sequentially in a time frame that is small compared to the time over which molecules migrate on the cell could also be constructed.

Figure 3:
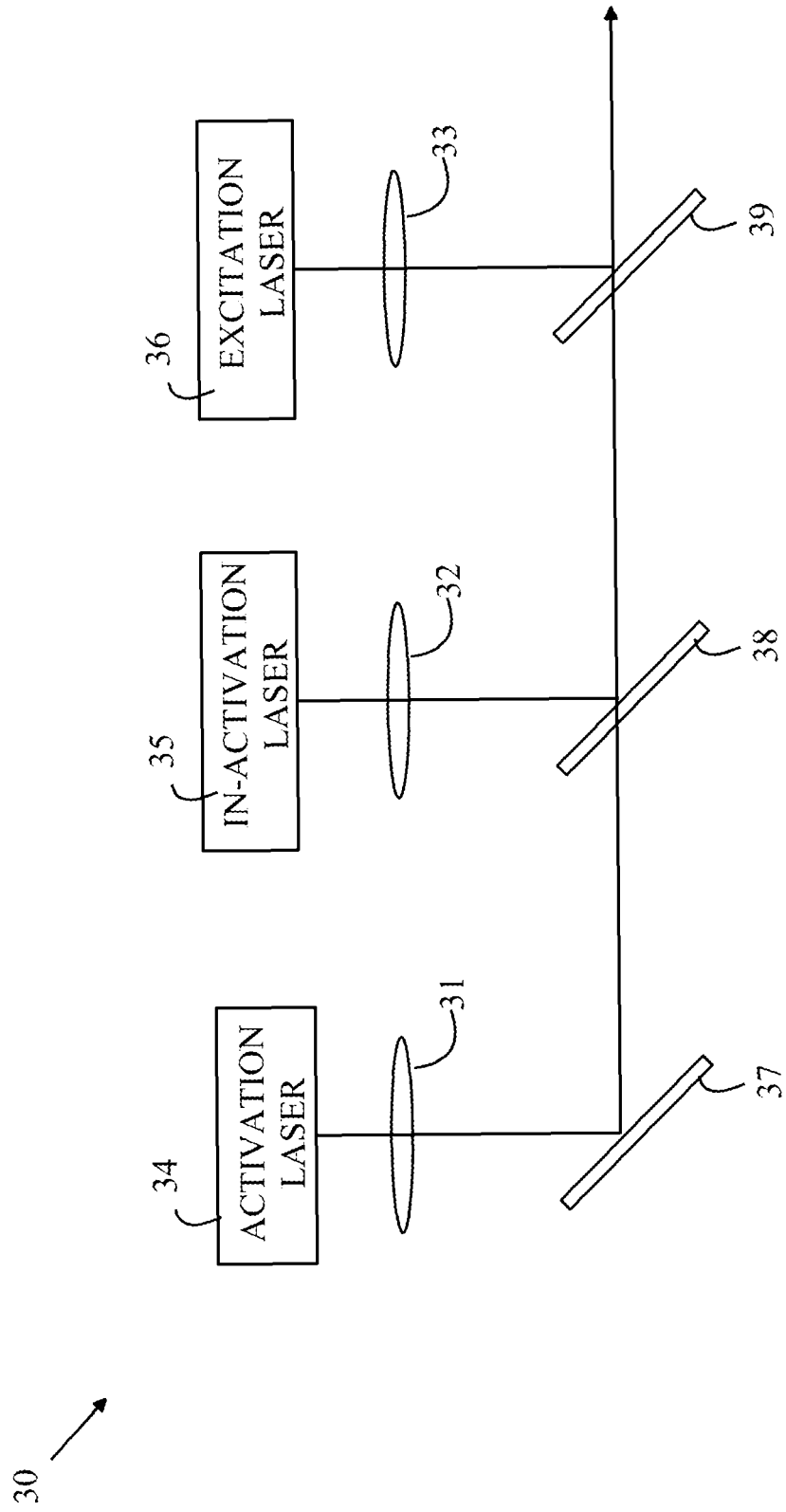
FIG. 3 illustrates one embodiment of a light source that can be utilized with the present invention to provide the desired illumination patterns.

Since the activation and inactivation illumination patterns are mutually exclusive, a separate imaging system must be provided for each pattern. Refer now to FIG. 3, which illustrates one embodiment of a light source that can be utilized with the present invention to provide the desired illumination patterns. Light source 30 includes three lasers 34-36 that generate light in the activation, inactivation, and excitation bands, respectively. The illumination pattern generated on the sample is controlled by an optical imaging assembly that operates in conjunction with the objective lens on the microscope. In FIG. 3, the optical assemblies are shown as simple lenses. However, it is to be understood that any assembly that generates the desired pattern from the corresponding laser could be utilized, e.g. combinations of lenses and apertures, or spatial light modulators. In the example shown in FIG. 3, the optical imaging assemblies corresponding to lasers 34-36 are shown at 37-39, respectively. While the imaging assemblies are shown as including lenses 31-33, it is to be understood that any suitable imaging system for processing the laser outputs to the desired geometry could be utilized.

The light from the activation and inactivation lasers is combined into a single beam by reflector 37 and dichroic reflector 38, which lets light of the wavelengths generated by activation laser 34 pass while reflecting light of the wavelengths generated by inactivation laser 35. The light from excitation laser 36 is likewise directed to the objective lens in the correct pattern by dichroic reflector 39, which lets light pass in both the inactivation and activation bands.

In one aspect of the invention, the dichroic beam splitter used to reflect the image of the sample onto the camera lets the three wavelengths discussed above pass through while reflecting a significant fraction of the light in the emission band of the fluorescent dyes. Dichroic beam splitters having multiple transmission windows are known to the art, and hence, will not be discussed in detail here. An example of a commercially-available device is the Semrock BrightLine quad-edge laser-flat dichroic beam splitter.

Figure 4:
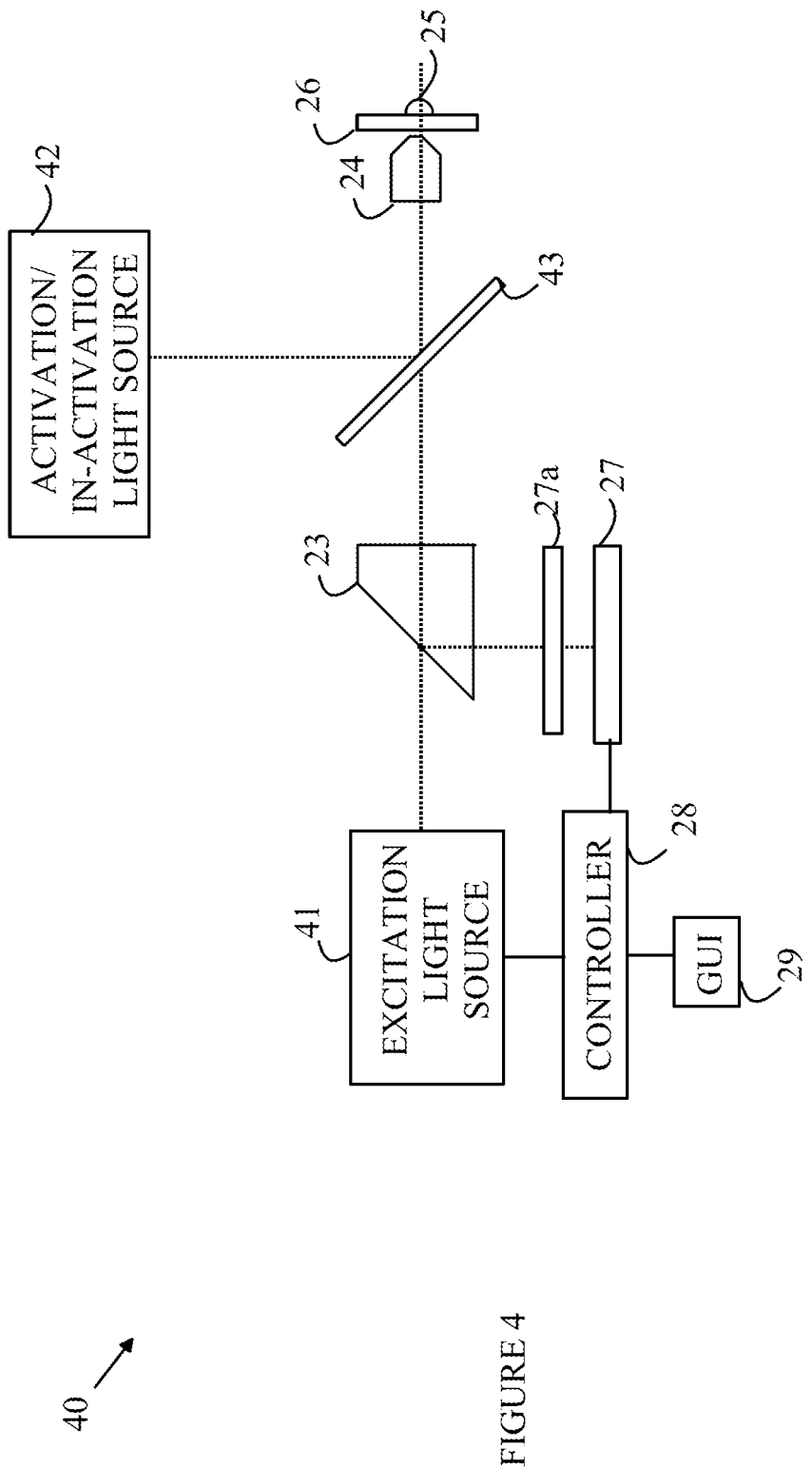
FIG. 4 illustrates another embodiment of the microscope according to the present invention.

Embodiments that do not require a dichroic beam splitter with multiple transmission windows can also be constructed. Refer now to FIG. 4, which illustrates another embodiment of the microscope according to the present invention. Microscope 40 utilizes an excitation light source that is imaged onto the sample 25 through dichroic beam splitter 23, which only requires a single transmission window for the excitation wavelength. An activation/inactivation light source 42 couples the activation/inactivation light pattern onto sample 25 via a partially-reflecting mirror 43 that allows the light from the excitation light source 41 to also reach the sample. The light from sample 25 during the examination of the cells after activation/inactivation will be reduced by the reflectivity of partially-reflecting mirror 43. However, since the lasers in activation/inactivation light source 42 can be increased in power output to compensate for the losses from partially-reflecting mirror 43, the fraction of the light striking partially-reflecting mirror 43 that is to be reflected into objective lens 24 can be significantly reduced. For example, if partially-reflecting mirror 43 has a reflectivity of 10 percent, the light lost due to the imposition of partially-reflecting mirror 43 during the examination of the cells with the excitation light source is acceptable. However, a suitable emission filter 27a can be placed in front of the camera to filter out any reflected activation/inactivation light that is reflected from various surfaces and arrives at the camera.

The above-described embodiments of the present invention utilize an annular inactivation region that surrounds a circular activation region; however, other patterns could be utilized. The particular pattern described above is easily generated from relatively simple optical elements, and hence, is advantageous. However, the method of the present invention only depends on forming adjacent regions in which the dye molecules are active and inactive, respectively. Any arrangement in which the molecules that are tagged with the active dye can be followed as those molecules are diluted by the molecules tagged with the inactive dye could be utilized.

In the above-described embodiments, the sample is not imaged during the activation/inactivation illumination. However, it may be advantageous to image the sample during this step to determine the boundaries of the activation and inactivation regions. For dyes that are not activated or inactivated by the excitation wavelength at the intensity used to view the sample, this imaging step can be accomplished by simultaneously illuminating the sample with light of the excitation wavelength. This arrangement also allows the operator to verify the activation of the dye molecules in the active region.

Examples of dyes that can be used are proteins such as Dendra, EosFP, Dronpa, PA-GFP, PA-mCherry, rsCherryRev, PA-mRFP1-1, kikGR, Kaede, Padron, reCherry, rdFastLime, PS-CFP2, Cyanine dyes (GE Healthcare) such as Cy3 or Cy5 (in pairs or alone), and Alexa Fluor (Invitrogen) or ATTO dyes (Atto-tec).

The above-described embodiments utilize a single dye. However, the method of the present invention can be practiced with multiple dyes. In a two-dye experiment, a second group of molecules in the sample is tagged with a second dye. The second dye has an active state that is generated by exposing said second dye to light of an activation wavelength and an inactive state that is generated by exposing said second dye to light of an inactivation wavelength. The second dye emits light of a wavelength different from the first dye when illuminated with an excitation wavelength. It should be noted that, in principle, all of the wavelengths could be different as long as there are no conflicts, e.g. one inactivation wavelength being the other molecule's activation wavelength, etc. In this embodiment, the ratios of intensities of light from the first and second dyes are measured. A two-color experiment allows the operator to gain information on the interaction of two different species of biomolecules including generating a measure of the co-localization of the different species of molecules as a function of time. Each species can be selectively labeled with a specific color, e.g. through immunostaining or genetic engineering.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. A method for measuring the mobility of molecules comprising:
   tagging first molecules in a sample with a first dye, said first dye having an active state that is generated by exposing said first dye to light of an activation wavelength and an inactive state that is generated by exposing said first dye to light of an inactivation wavelength;
   simultaneously illuminating said sample with light in first and second regions in a microscope with a light pattern in which said first dye is activated by light of an excitation wavelength and substantially all of said molecules tagged with said first dye in said first region are in said active state and in which said first dye is inactivated by light of an inactivation wavelength and substantially all of said molecules tagged with said first dye in said second region are in said inactive state, to generate regions of activated and inactivated first molecules; and
   recording an image of said activated first molecules while said sample is no longer illuminated by said light pattern and when said first molecules are illuminated with light of an excitation wavelength, wherein molecules having said first dye in said inactive state are distinguishable from molecules having said first dye in said active state in said microscope when illuminated with light of said excitation wavelength.

2. The method of claim 1 wherein said recorded image includes part of said second region.

3. The method of claim 1 wherein recording said image comprises using a filter to distinguish dye molecules in said active state from dye molecules in said inactive state.

4. The method of claim 1 wherein recording said image comprises distinguishing said dye molecules in said active state from dye molecules in said inactive state based on a difference in intensity of light emitted by said dye molecules in said active and inactive states.

5. The method of claim 1 wherein said recording an image comprises recording a first image of said sample after a first time after illuminating said sample with said light pattern, said first time being chosen such that activated first molecules have moved a sufficient distance to allow individual activated first molecules, or clusters of activated first molecules to be viewed separately with said microscope.

6. The method of claim 5 further comprising recording a second image of said sample illuminated by said excitation wavelength at a second time, said first time differing from said second time by an amount sufficient to detect motion of said activated first molecules in said sample.

7. The method of claim 5 further comprising measuring an intensity of light from one of said molecules or cluster of first molecules in said first image.

8. The method of claim 5 further comprising
   tagging second molecules in said sample with a second dye, said second dye having an active state that is generated by exposing said second dye to light of an activation wavelength and an inactive state that is generated by exposing said second dye to light of an inactivation wavelength, said second dye emitting light of a wavelength different from said first dye when illuminated with an excitation wavelength; and
   measuring a ratio of intensities of light from said first and second dyes in said first image.

9. The method of claim 8 further comprising generating a measure of a co-localization of said first and second molecules.

10. The method of claim 1 wherein said first region is surrounded by said second region.

11. The method of claim 1 wherein said first dye is chosen from the group consisting of proteins Dendra, EosFP, Dronpa, PA-GFP, PA-mCherry, rsCherryRev, PA-mRFP1-1, kikGR, Kaede, Padron, reCherry, rdFastLime, PS-CFP2, Cyanine dyes, and Alexa Fluor and ATTO dyes.

12. A microscope comprising:
   a light source for illuminating a sample to be viewed in said microscope, said light source generating light of an activation wavelength, light of an inactivation wavelength, and light of an excitation wavelength, said activation wavelength, and inactivation wavelength being different from one another;
   a camera that records an image of said sample when said sample is illuminated with light of said excitation wavelength; and
   an imaging system that illuminates said sample simultaneously with light in first and second regions in a first pattern having said first region illuminated with said activation wavelength and in said second region illuminated with said inactivation wavelength, said first and second regions being adjacent to one another.

13. The microscope of claim 12 wherein said excitation wavelengths are different from said activation and inactivation wavelengths.

14. The microscope of claim 12 further comprising a controller that first illuminates said sample with said first pattern and then illuminates said sample with said excitation wavelength in both said first and second regions.

15. The microscope of claim 12 wherein said first region is surrounded by said second region.

16. The microscope of claim 15 wherein said second region comprises an annular region and said first region comprises a circular region.

17. The microscope of claim 12 further comprising a dichroic beam splitter that separates light of said activation wavelength, inactivation wavelength, and excitation wavelength from light generated by said sample when said sample is illuminated with light of said excitation wavelength.

18. The microscope of claim 12 further comprising a dichroic beam splitter that transmits light of said activation wavelength, inactivation wavelength, and excitation wavelength while reflecting light generated by said sample when said sample is illuminated with light of said excitation wavelength.

* * * * *